US009750571B2

(12) United States Patent
Paulus et al.

(10) Patent No.: US 9,750,571 B2
(45) Date of Patent: *Sep. 5, 2017

(54) RE-HYDRATION ANTENNA FOR ABLATION

(71) Applicant: COVIDIEN LP, Mansfield, MA (US)

(72) Inventors: Joseph A. Paulus, Lafayette, CO (US); Arnold V. DeCarlo, Frederick, CO (US); Casey M. Ladtkow, Erie, CO (US); Behzad Ghorbani-Elizeh, Boulder, CO (US); Brandon C. Gay, Superior, CO (US)

(73) Assignee: COVIDIEN LP, Mansfield, MA (US)

( * ) Notice: Subject to any disclaimer, the term of this patent is extended or adjusted under 35 U.S.C. 154(b) by 12 days.

This patent is subject to a terminal disclaimer.

(21) Appl. No.: 14/954,980

(22) Filed: Nov. 30, 2015

(65) Prior Publication Data
US 2016/0081748 A1 Mar. 24, 2016

Related U.S. Application Data

(63) Continuation of application No. 12/413,023, filed on Mar. 27, 2009, now Pat. No. 9,198,723.
(Continued)

(51) Int. Cl.
*A61B 18/18* (2006.01)
*A61N 5/00* (2006.01)
*A61B 18/00* (2006.01)

(52) U.S. Cl.
CPC .......... *A61B 18/1815* (2013.01); *A61B 18/18* (2013.01); *A61B 2018/00029* (2013.01);
(Continued)

(58) Field of Classification Search
CPC ................ A61B 18/18; A61B 18/1815; A61B 2018/00011; A61B 2018/00029;
(Continued)

(56) References Cited

U.S. PATENT DOCUMENTS 3,631,363 A   12/1971  Miller
4,397,313 A    8/1983  Vaguine
(Continued)

FOREIGN PATENT DOCUMENTS

DE       390937 C    3/1924
DE      1099658 B    2/1961
(Continued)

OTHER PUBLICATIONS

Australian Examination Report from Appl. No. AU2015203459 dated Jul. 21, 2016.
(Continued)

*Primary Examiner* — Bhisma Mehta
*Assistant Examiner* — Larry R Wilson

(57) ABSTRACT

A system for use with a microwave antenna includes a microwave antenna configured to deliver microwave energy from a power source to tissue and a sensor module in operative communication with the power source and configured to detect a reflectance parameter. The system further includes a jacket adapted to at least partially surround the microwave antenna to define a fluid channel between the jacket and the microwave antenna. A plurality of fluid distribution ports are defined through the jacket and are in fluid communication with the fluid channel to permit the flow of fluid through the jacket. The system further includes a fluid pumping system operably coupled to the power source and configured to selectively provide cooling fluid to the fluid channel for distribution through the fluid distribution ports based on the reflectance parameter.

16 Claims, 9 Drawing Sheets

Related U.S. Application Data

(60) Provisional application No. 61/041,072, filed on Mar. 31, 2008.

(52) U.S. Cl.
CPC .............. *A61B 2018/00035* (2013.01); *A61B 2018/00577* (2013.01); *A61B 2018/1823* (2013.01); *A61N 2005/005* (2013.01); *A61N 2005/007* (2013.01)

(58) Field of Classification Search
CPC  A61B 2018/00035; A61B 2018/00577; A61B 2018/1823; A61N 5/022; A61N 5/045; A61N 2005/005; A61N 2005/007
See application file for complete search history.

(56) References Cited

U.S. PATENT DOCUMENTS

| | | |
|---|---|---|
| 4,462,412 A | 7/1984 | Turner |
| 4,572,190 A | 2/1986 | Azam et al. |
| 4,798,215 A | 1/1989 | Turner |
| 4,800,899 A | 1/1989 | Elliott |
| 5,097,844 A | 3/1992 | Turner |
| 5,344,435 A | 9/1994 | Turner et al. |
| 5,417,210 A | 5/1995 | Funda et al. |
| 5,472,441 A | 12/1995 | Edwards et al. |
| 5,620,480 A | 4/1997 | Rudie |
| 5,735,847 A | 4/1998 | Gough et al. |
| 5,843,021 A | 12/1998 | Edwards et al. |
| 6,002,968 A | 12/1999 | Edwards |
| 6,031,375 A | 2/2000 | Atalar et al. |
| 6,059,780 A | 5/2000 | Gough et al. |
| 6,350,276 B1 | 2/2002 | Knowlton |
| 6,375,606 B1 | 4/2002 | Garibaldi et al. |
| 6,413,255 B1 | 7/2002 | Stern |
| 6,416,491 B1 | 7/2002 | Edwards et al. |
| 6,425,912 B1 | 7/2002 | Knowlton |
| 6,427,089 B1 | 7/2002 | Knowlton |
| 6,490,488 B1 | 12/2002 | Rudie et al. |
| 6,514,251 B1 | 2/2003 | Ni et al. |
| 6,603,994 B2 | 8/2003 | Wallace et al. |
| 6,725,080 B2 | 4/2004 | Melkent et al. |
| 6,866,624 B2 | 3/2005 | Chornenky et al. |
| 7,070,595 B2 | 7/2006 | Ormsby et al. |
| 7,278,991 B2 | 10/2007 | Morris et al. |
| 7,294,127 B2 | 11/2007 | Leung et al. |
| 7,311,703 B2 | 12/2007 | Turovskiy et al. |
| 7,422,586 B2 | 9/2008 | Morris et al. |
| 7,439,736 B2 | 10/2008 | Meaney et al. |
| 7,467,015 B2 | 12/2008 | van der Weide |
| 7,565,207 B2 | 7/2009 | Turner et al. |
| 9,198,723 B2 | 12/2015 | Paulus et al. |
| 2002/0022836 A1 | 2/2002 | Goble et al. |
| 2002/0120261 A1 | 8/2002 | Morris et al. |
| 2004/0097805 A1 | 5/2004 | Verard et al. |
| 2004/0242992 A1 | 12/2004 | Hareyama |
| 2005/0015081 A1* | 1/2005 | Turovskiy .............. A61B 18/18 606/33 |
| 2005/0137662 A1 | 6/2005 | Morris et al. |
| 2005/0245920 A1 | 11/2005 | Vitullo et al. |
| 2006/0171506 A1* | 8/2006 | Lovoi .................. A61N 5/1002 378/130 |
| 2006/0287649 A1 | 12/2006 | Ormsby et al. |
| 2007/0016180 A1 | 1/2007 | Lee et al. |
| 2007/0077230 A1 | 4/2007 | Mon |
| 2007/0203551 A1 | 8/2007 | Cronin et al. |
| 2008/0161890 A1* | 7/2008 | Lafontaine ......... A61B 18/1492 607/105 |
| 2008/0319434 A1 | 12/2008 | Rick et al. |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 481 685 A1 | 4/1992 |
| EP | 0 521 264 A2 | 1/1993 |
| EP | 0541930 A1 | 5/1993 |
| EP | 0 556 705 A1 | 8/1993 |
| EP | 0 558 429 A1 | 9/1993 |
| EP | 0572131 A1 | 12/1993 |
| EP | 0 836 868 A2 | 4/1998 |
| EP | 1278007 A1 | 1/2003 |
| EP | 1159926 A3 | 3/2003 |
| EP | 1 810 627 A1 | 7/2007 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 | 3/1996 |
| JP | 08252263 A | 10/1996 |
| JP | 03010223 | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029563 A | 2/2001 |
| JP | 2001128990 A | 5/2001 |
| SU | 166452 | 1/1965 |
| SU | 401367 A1 | 10/1973 |
| SU | 727201 A2 | 4/1980 |
| WO | 97/41924 A1 | 11/1997 |
| WO | 97/43971 A2 | 11/1997 |
| WO | 00/48672 A1 | 8/2000 |

(56) References Cited

FOREIGN PATENT DOCUMENTS

| WO | 00/51513 | A1 | 9/2000 |
|---|---|---|---|
| WO | 01/01847 | A1 | 1/2001 |
| WO | 01/74252 | A2 | 10/2001 |
| WO | 02/45790 | A2 | 6/2002 |
| WO | 02/061880 | A2 | 8/2002 |
| WO | 2004/112628 | A1 | 12/2004 |
| WO | 2005/016119 | A2 | 2/2005 |
| WO | 2007/076924 | A2 | 7/2007 |

OTHER PUBLICATIONS

European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Cosman et al., "Methods of Making Nervous System Lesions" in William RH, Rengachary SS (eds): Neurosurgery, New York: McGraw.cndot.Hill, vol. 111, (1984), pp. 2490-2499.
Crawford et al., "Use of the LigaSure.TM. Vessel Sealing System in Urologic Cancer Surger" Grand Rounds in Urology 1999, vol. 1, Issue 4, pp. 10-17.

(56) References Cited

OTHER PUBLICATIONS

Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages, Nov. 1, 2003.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure.TM. Vessel Sealing System for Peri-Hilar Vessels in Laparoscopic Nephrectomy" Sales/Product Literature 2000.
Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12:876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M.A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTech product literature (Mar. 2000) I'D Wire: product description, 1 page.
MDTech product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.

(56) References Cited

OTHER PUBLICATIONS

Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thennoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
S. Humphries Jr. et al., "Finite-Element Codes to Model Electrical Heating and Non.cndot.Llnear Thermal Transport in Biological Media", Proc. ASME HTD-355, 131 (1997).

Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electrosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/USO4/04685 dated Aug. 27, 2004.
International Search Report PCT/USO4/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Internation Search Report EP 09 15 6861 dated Aug. 4, 2009.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
Australian Patent Examination Report No. 1 from AU Appl. No. 2009201253 dated Feb. 8, 2013.
Australian Patent Examination Report No. 1 from AU Appl. No. 2013242809 dated Dec. 1, 2014.
Canadian Office Action from Appl. No. 2,660,930 dated Oct. 7, 2015.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
Lyndon 13. Johnson Space Center, Houston, Texas, "Compact Directional Microwave Antenna for Localized Heating," NASA Tech Briefs, Mar. 2008.
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.

(56) References Cited

OTHER PUBLICATIONS

U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.

* cited by examiner

RE-HYDRATION ANTENNA FOR ABLATION

CROSS-REFERENCE TO RELATED APPLICATIONS

The present application is a continuation application of U.S. patent application Ser. No. 12/413,023, filed on Mar. 27, 2009, which claims priority to U.S. Provisional Application No. 61/041,072 filed on Mar. 31, 2008, the entire contents of each of which are incorporated herein by reference.

BACKGROUND

Technical Field

The present disclosure relates generally to devices that may be used in tissue ablation procedures. More particularly, the present disclosure relates to devices and methods for maintaining ablation temperatures surrounding microwave antennas radiofrequency probes during ablation procedures.

Background of Related Art

In the treatment of diseases such as cancer, certain types of cancer cells have been found to denature at elevated temperatures which are slightly lower than temperatures normally injurious to healthy cells. These types of treatments, known generally as hyperthermia therapy, typically utilize electromagnetic radiation to heat diseased cells to temperatures above 41° Celsius while maintaining adjacent healthy cells at lower temperatures where irreversible cell destruction will not occur. Other procedures utilizing electromagnetic radiation to heat tissue also include ablation and coagulation of the tissue. Such ablation procedures, e.g., such as those performed for menorrhagia, are typically done to ablate and coagulate the targeted tissue to denature or kill the tissue. Many procedures and types of devices utilizing electromagnetic radiation therapy are known in the art. Such therapy is typically used in the treatment of tissue and organs such as the prostate, heart, kidney, lung, brain, and liver.

Presently, there are several types of microwave probes in use, e.g., monopole, dipole, and helical, which may be inserted into a patient for the treatment of tumors by heating the tissue for a period of time sufficient to cause cell death and necrosis in the tissue region of interest. Such microwave probes may be advanced into the patient, e.g., laparoscopically or percutaneously, and into or adjacent to the tumor to be treated. The probe is sometimes surrounded by a dielectric sleeve.

However, in transmitting the microwave energy into the tissue, the outer surface of the microwave antenna typically may heat up and unnecessarily desiccate, or even necrose, healthy tissue immediately adjacent the antenna outer surface. This creates a water or tissue phase transition (steam) that allows the creation of a significant additional heat transfer mechanism as the steam escapes from the local/active heating area and re-condenses further from the antenna. The condensation back to water deposits significant energy further from the antenna/active treatment site. This local tissue desiccation occurs rapidly resulting in an antenna impedance mismatch, which both limits power delivery to the antenna and effectively eliminates steam production/phase transition as a heat transfer mechanism for tissue ablation.

To prevent the charring of adjacent tissue, several different cooling methodologies are conventionally employed. For instance, some microwave antennas utilize balloons which are inflatable around selective portions of the antenna to cool the surrounding tissue. Thus, the complications associated with tissue damaged by the application of microwave radiation to the region are minimized. Typically, the cooling system and the tissue are maintained in contact to ensure adequate cooling of the tissue.

Other devices attempt to limit the heating of tissue adjacent the antenna by selectively blocking the propagation of the microwave field generated by the antenna. These cooling systems also protect surrounding healthy tissues by selectively absorbing microwave radiation and minimizing thermal damage to the tissue by absorbing heat energy.

SUMMARY

The present disclosure provides a system for use with a microwave antenna including a microwave antenna configured to deliver microwave energy from a power source to tissue and a sensor module in operative communication with the power source and configured to detect a reflectance parameter. The system further includes a jacket adapted to at least partially surround the microwave antenna to define a fluid channel between the jacket and the microwave antenna. A plurality of fluid distribution ports are defined through the jacket and are in fluid communication with the fluid channel to permit the flow of fluid through the jacket. The system further includes a fluid pumping system operably coupled to the power source and configured to selectively provide cooling fluid to the fluid channel for distribution through the fluid distribution ports based on the reflectance parameter.

In another embodiment, a system for use with a microwave antenna includes a microwave antenna configured to deliver microwave energy from a power source to tissue and a temperature sensor operably coupled to the microwave antenna and configured to detect at least one of a tissue temperature and an antenna temperature. The system further includes a jacket adapted to at least partially surround the microwave antenna to define a fluid channel between the jacket and the microwave antenna. A plurality of fluid distribution ports are defined through the jacket and are in fluid communication with the fluid channel to permit the flow of fluid through the jacket. The system further includes a fluid pumping system operably coupled to the power source and configured to selectively provide cooling fluid to the fluid channel for distribution through the fluid distribution ports based on a comparison between the detected temperature and a predetermined temperature.

The present disclosure also provides for a method for impedance matching during an ablation procedure. The method includes the initial steps of applying microwave energy from an antenna to tissue and detecting a reflectance parameter. The method also includes the steps of analyzing the reflectance parameter to determine an impedance mismatch and selectively expelling an amount of fluid from the antenna into the tissue based on the mismatch. The method further includes the step of repeating the step of analyzing the reflectance parameter.

In another embodiment of the present disclosure, a method for regulating temperature of tissue undergoing ablation includes the initial steps of applying microwave energy from an antenna to tissue and providing a temperature sensor to detect at least one of a tissue temperature and an antenna temperature. The method also includes the steps of comparing the detected temperature with a predetermined temperature and selectively expelling an amount of fluid from the antenna into the tissue based on the comparison between the detected temperature and the predetermined temperature. The method further includes the step of repeating the step of comparing the detected temperature with a predetermined temperature.

In another embodiment of the present disclosure, a method for regulating temperature of tissue undergoing ablation includes the initial steps of applying microwave energy from an antenna to tissue and detecting at least one of a tissue temperature and an antenna temperature. The method also includes the steps of comparing the detected temperature with a predetermined temperature and selectively expelling an amount of fluid from the antenna into the tissue based on the comparison between the detected temperature and the predetermined temperature. The method also includes the step of repeating the step of comparing the detected temperature with a predetermined temperature.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
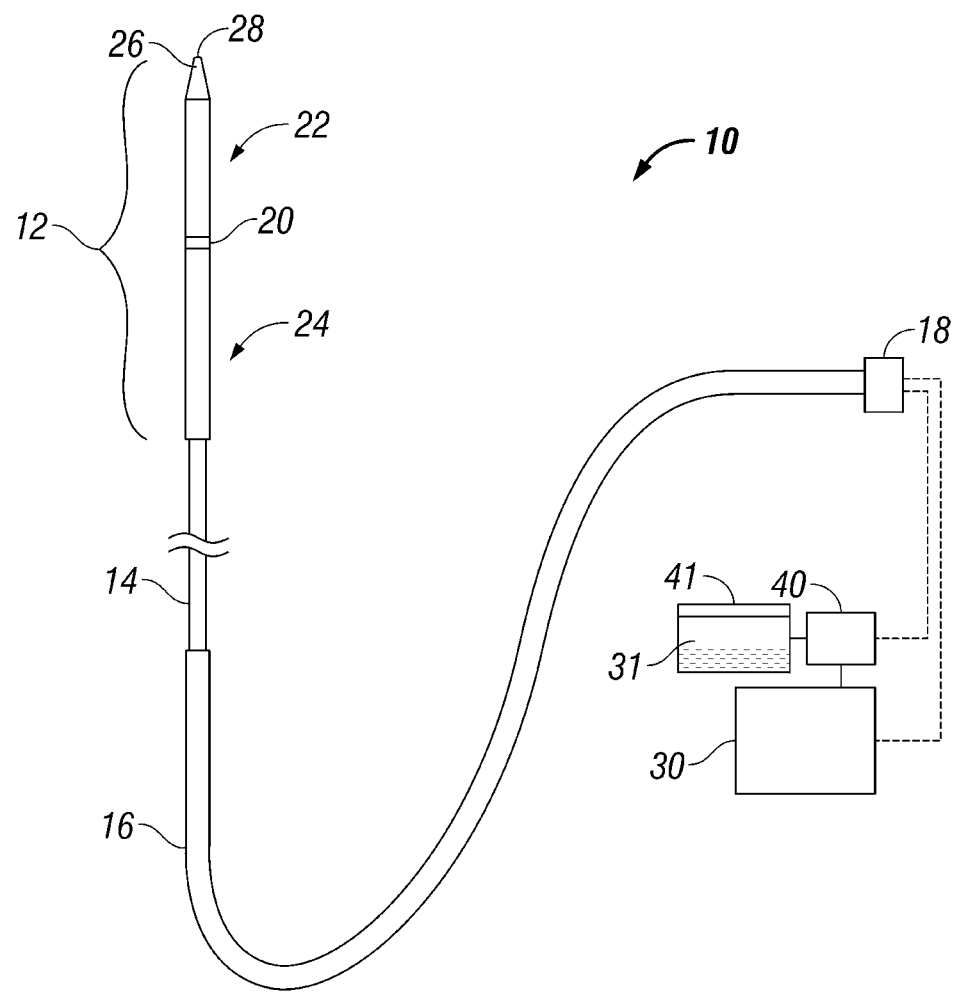
FIG. 1 is a schematic diagram of a microwave antenna assembly according to an embodiment of the present disclosure.

In the drawings and in the description that follows, the term "proximal", as is traditional, will refer to the end of the apparatus that is closest to the clinician, while the term "distal" will refer to the end that is furthest from the clinician.

Microwave or radiofrequency ablation is capable of causing significant temperature elevations and desiccation of tissue surrounding the applicator. This elevation of temperature creates a water or tissue phase transition by which steam escapes from the active heating area and recondenses further from the applicator. In this way, the tissue phase transition effectively serves as a heat transfer mechanism. As well as adding a new heat transfer mechanism, the movement of water, and, specifically, the loss of water in some volumes of tissue are expected to affect other tissue properties, such as impedance. Changes in tissue thermal properties directly affects the heat conduction within tissue and changes tissue dielectric properties that lead to changes in the location of energy deposition within the targeted, as well as the surrounding tissues. That is, the condensation back to water deposits significant energy further from the active heating area. However, the desiccation of tissue surrounding the applicator effectively eliminates steam production as a heat transfer mechanism and as a result, the temperature of the active heating area significantly elevates to cause an impedance mismatch.

The present disclosure provides for a system and method to re-hydrate tissue undergoing treatment through use of various ablation apparatuses (e.g., a microwave antenna, radiofrequency probe, pump, etc.), which compensates for the power imbalance and/or impedance mismatch that are inherent with dynamic tissue changes. In particular, hydration of tissue may be achieved utilizing cooling systems in which cooling fluid is circulated through and expelled from a microwave antenna or radiofrequency probe. The following disclosure is directed towards a microwave antenna application; however, teachings of the present disclosure may be applied to other types of ablation devices, such as radiofrequency probes, or even ultrasonic and laser tissue treatment devices.

FIG. 1 shows a diagram of an ablation antenna assembly 10 that may be any type of probe suitable for delivering microwave energy and may be used with a cooling system as described herein. The antenna assembly 10 generally includes a radiating portion 12 that may be coupled by feedline 14 (or shaft) via conduit 16 to connector 18, which may further connect the assembly 10 to a power generating source 30 (e.g., a generator) and a supply pump 40.

Assembly 10 includes a dipole ablation probe assembly. Other antenna assemblies, e.g., monopole or leaky wave antenna assemblies, may also be utilized. Distal portion 22 of radiating portion 12 may include a tapered end 26 that terminates at a tip 28 to allow for insertion into tissue with minimal resistance. In those cases where the radiating portion 12 is inserted into a pre-existing opening, tip 28 may be rounded or flat.

Junction member 20 is located between proximal portion 24 and distal portion 22 such that a compressive force may be applied by distal and proximal portions 22, 24 upon junction member 20. Placing distal and proximal portions 22, 24 in a pre-stressed condition prior to insertion into tissue enables assembly 10 to maintain a stiffness that is sufficient to allow for unaided insertion into the tissue while maintaining a minimal antenna diameter, as described in detail below.

Feedline 14 electrically connects antenna assembly 10 via conduit 16 to generator 30 and typically includes a coaxial cable (not explicitly shown) made of a conductive metal, which may be semi-rigid or flexible. Feedline 14 may also have a variable length from a proximal end of radiating portion 12 to a distal end of conduit 16 ranging between about 1 to 15 inches. The feedline 14 may be constructed of copper, gold, stainless steel or other conductive metals with similar conductivity values. The metals may also be plated with other materials, e.g., other conductive materials, to improve conductivity or decrease energy loss, or for other purposes known in the art.

Figure 2:
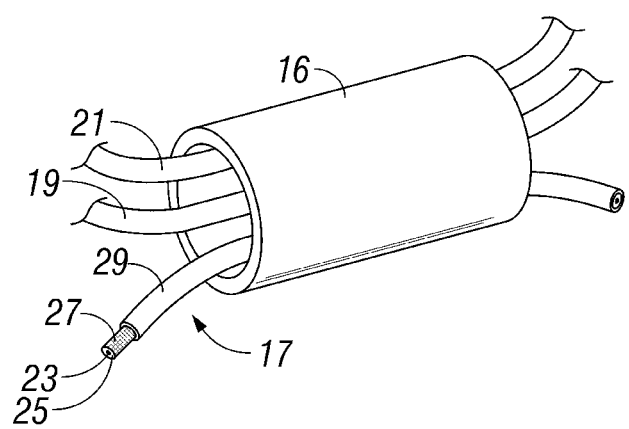
FIG. 2 is a perspective view of the microwave antenna assembly of FIG. 1 having a conduit defined therein.

As shown in FIG. 2, conduit 16 includes a flexible coaxial cable 17 and one or more flexible tubes, namely, inflow tubing 19 and outflow tubing 21 for supplying and withdrawing cooling liquid 31 into and out of radiating portion 12, respectively. Cable 17 includes an inner conductor 23 (e.g., wire) surrounded by an insulating spacer 25, which is concentrically disposed within an outer conductor 27 (e.g., cylindrical conducting sheath). Cable 17 may also include an outer insulating sheath 29 surrounding the outer conductor 27. Connector 18 couples the inflow tubing 19 and outflow tubing 21 to the supply pump 40 and the cable 17 to the generator 30. The supply pump 40 is coupled to a supply tank 41 (FIG. 1) that stores cooling liquid 31 and maintains the liquid at a predetermined temperature (e.g., ambient room temperature). In one embodiment, the supply tank 41 may include a cooling unit that cools the returning cooling liquid 31 from the outflow tubing 19.

The cooling fluid 31 may be pumped using positive pressure through inflow tubing 19. Alternatively, negative pressure may also be used to draw the cooling fluid 31 out of the region through outflow tubing 21. Negative pressure through outflow tubing 21 may be utilized either alone or in conjunction with positive pressure through inflow tubing 19. Alternatively, positive pressure through inflow tubing 19 may be utilized either alone or in conjunction with negative pressure through outflow tubing 21. In pumping the cooling fluid 31, the cooling fluid 31 may be passed at a constant flow rate. In another variation, the flow may be intermittent such that a volume of cooling fluid 31 may be pumped into the radiating portion 12 and allowed to warm up by absorbing heat from the antenna. Once the temperature of the cooling fluid 31 reaches a predetermined level below temperatures where thermal damage to tissue occurs, the warmed fluid may be removed and displaced by additional cooling fluids.

The cooling fluid 31 used may vary depending upon desired cooling rates and the desired tissue impedance matching properties. Biocompatible fluids may be included that have sufficient specific heat values for absorbing heat generated by radio frequency ablation probes, e.g., liquids including, but not limited to, water, saline, liquid chlorodifluoromethane, etc. In another variation, gases (such as nitrous oxide, nitrogen, carbon dioxide, etc.) may also be utilized as the cooling fluid 31. For example, an aperture defined within the radiating portion 12 may be configured to take advantage of the cooling effects from the Joule-Thompson effect, in which case a gas, e.g., nitrous oxide, may be passed through the aperture to expand and cool the radiating portion 12. In yet another variation, a combination of liquids and/or gases, as mentioned above, may be utilized as the cooling medium.

Figure 3:
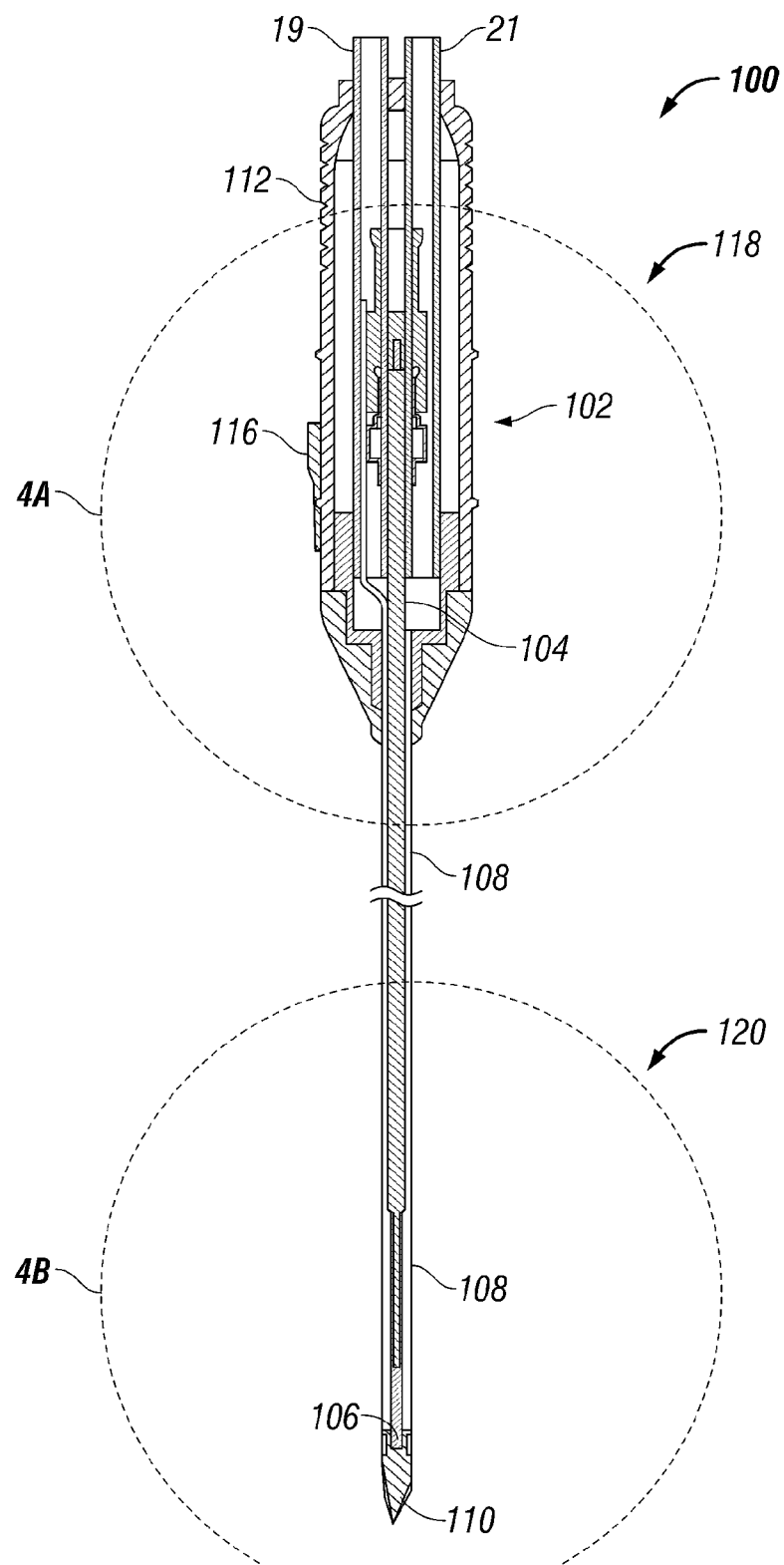
FIG. 3 is a cross-sectional view of a microwave antenna according to one embodiment of the present disclosure.

FIG. 3 show a cross-sectional side view and an end view, respectively, of one variation of the antenna assembly 10 (e.g., cooling assembly 100) that may be utilized with any number of conventional ablation probes (or the ablation probes described herein), particularly the straight probe configuration as shown in FIG. 1. Although this variation illustrates the cooling of a straight probe antenna, a curved or looped ablation probe may also utilize much of the same or similar principles, as further described below.

Cooling assembly 100 includes a cooling handle assembly 102 and an elongated outer jacket 108 extending from handle assembly 102. As will be described in further detail below, a plurality of fluid distribution ports 114 (FIG. 4B) are defined through the thickness of outer jacket 108 to facilitate the introduction of cooling fluid 31 from the cooling assembly 100 into surrounding tissue. Outer jacket 108 extends and terminates at tip 110, which may be tapered to a sharpened point to facilitate insertion into and manipulation within tissue, if necessary. Antenna 104 is positioned within handle assembly 102 such that the radiating portion 106 of antenna 104 extends distally into outer jacket 108 towards tip 110. Inflow tubing 19 extends into a proximal end of handle body 112 and distally into a portion of outer jacket 108. Outflow tubing 21 extends from within handle body 112 such that the distal ends of inflow tubing 19 and outflow tubing 21 are in fluid communication with one another, as described in further detail below.

Figure 4A:
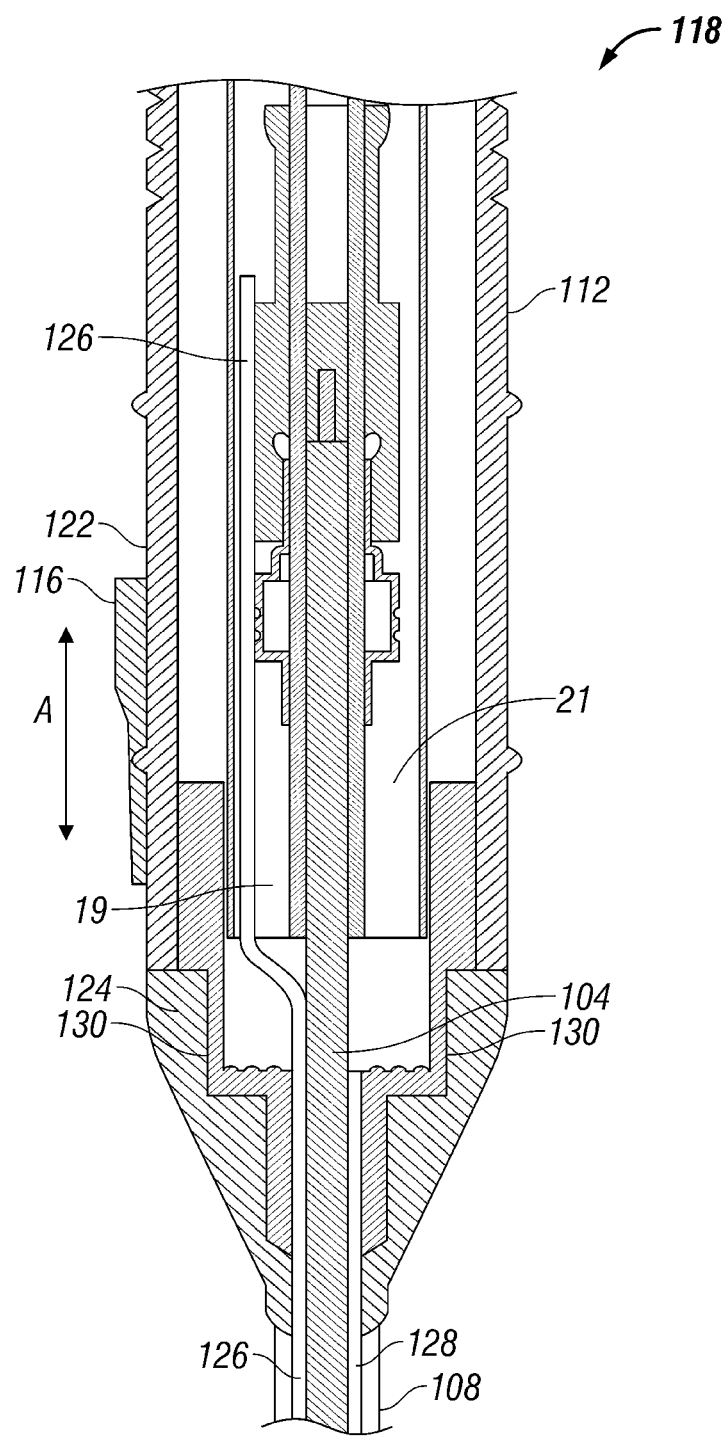
FIGS. 4A and 4B are enlarged views of the areas of detail of the microwave antenna of FIG. 3.

FIG. 4A shows handle assembly detail 118 from FIG. 3. As shown, handle body 112 includes proximal handle hub 122, which encloses a proximal end of antenna 104, and distal handle hub 124, which may extend distally to engage outer jacket 108. Proximal handle hub 122 and distal handle hub 124 are configured to physically interfit with one another at hub interface 130 to form a fluid tight seal. Accordingly, proximal handle hub 122 may be configured to be received and secured within a correspondingly configured distal handle hub 124 (seen in FIG. 3 as a male-female connection). A slide button 116 is disposed on handle body 112 and operably coupled to a tube 140 disposed coaxially through at least a portion of outer jacket 108 (see FIGS. 4B and 4C). Movement of the slide button 116 relative to handle body 112, as depicted in FIG. 4A by bidirectional arrow A, translates corresponding movement of the tube 140 relative to an inner surface of outer jacket 108, as depicted in FIG. 4B by bidirectional arrow B, to facilitate the placement of cooling fluid and/or steam into surrounding tissue, as will be discussed in further detail below.

The distal ends of inflow tubing 19 and outflow tubing 21 may be positioned within the handle body 112 such that fluid is pumped into handle body 112 via the supply pump 40 through the inflow tubing 19. Cooling fluid 31 entering the handle body 112 comes into direct contact with at least a portion of the shaft of the antenna 104 to allow for convective cooling of the antenna shaft to occur. The cooling fluid 31 may be allowed to exit the handle body 112 via the outflow tubing 21. An additional inlet tube 126 is positioned within the antenna cooling assembly 100 to extend between the handle body 112 and the radiating portion 106 (FIG. 4B) of the antenna 104 and a corresponding outlet tube 128 may also extend between the handle body 112 and the radiating portion 106. The proximal end of the inlet tube 126 is in fluid communication with the inflow tubing 19 to allow the cooling fluid 31 to flow distally within the outer jacket 108 towards antenna radiating portion 106 (FIG. 4B). Alternatively, the inlet tube 126 and the outlet tube 128 may be omitted from the cooling assembly 100 and the outer jacket 108 may remain in direct fluid communication with the inflow tubing 19 and the outflow tubing 21 such that cooling fluid 31 contacts the antenna 104 directly along a portion of the length, or a majority of the length, or the entire length of the antenna 104. Thus, the cooling assembly 100 is effective in cooling the antenna 104 directly.

Figure 4B:
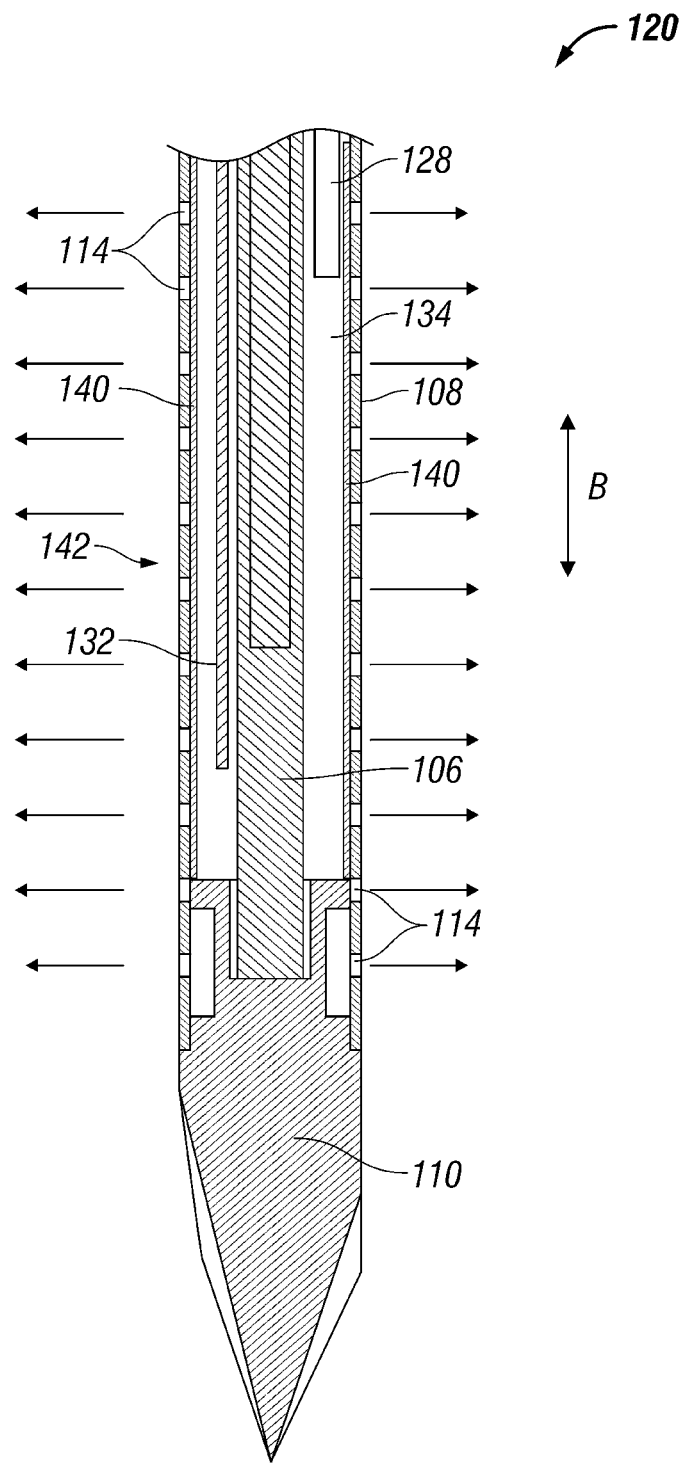

FIG. 4B shows outer jacket detail embodiment 120, from FIG. 3. The illustrated embodiment shows the distal end 132 of inlet tube 126, which extends distally through outer jacket 108. The opening at distal end 132 is positioned within outer jacket 108 near or at the distal end of outer jacket 108 such that distal end 132 opens to fluid channel 134. The cooling fluid 31 enters fluid channel 134 and fills the volume surrounding the radiating portion 106 and surrounding at least a portion of the antenna 104. As cooling fluid 31 enters fluid channel 134, the cooling fluid 31 is withdrawn through a distal opening in outlet tube 128, which is located proximally of distal end 132 to allow for increased convective cooling between the cooling fluid 31 and the antenna 104.

The cooling fluid 31 is pumped using positive pressure through inlet tube 126. Alternatively, negative pressure may also be used to draw the fluid out of the region through outlet tube 128. Negative pressure through outlet tube 128 may be utilized either alone or in conjunction with positive pressure through inlet tube 126. Alternatively, positive pressure through inlet tube 126 may be utilized either alone or in conjunction with negative pressure through outlet tube 128.

The cooling fluid 31 used may vary depending upon desired cooling rates and the desired tissue impedance matching properties. Biocompatible fluids having sufficient specific heat values for absorbing heat generated by microwave ablation antennas may be utilized, e.g., liquids including, but not limited to, water, saline, Fluorinert®, liquid chlorodifluoromethane, etc. (As is well-known, the material sold under the trademark Fluorinert is a perfluorocarbon fluid distributed commercially by Minnesota Mining and Manufacturing Company (3M), St. Paul, Minn., USA.)

The illustrated embodiment in FIG. 4B shows tube 140 and a plurality of fluid distribution ports 114 defined through the thickness of the outer jacket 108. The fluid distribution ports 114 enable cooling fluid 31 to be expelled from the fluid channel 134 into and/or proximate the target tissue. Tube 140 is disposed coaxially through at least a portion of outer jacket 108 such that fluid communication between one or more fluid distribution ports 114 and fluid channel 134 is selectively interrupted. More specifically, as tube 140 is moved from a distal most position (see FIGS. 4B and 4C) proximally relative to outer jacket 108 by corresponding proximal movement of slide button 116, an increasing number of fluid distribution ports 114 are exposed to fluid channel 134 from a distal end of fluid channel 134 toward a proximal end of fluid channel 134, to permit cooling fluid 31 to be expelled via the exposed fluid distribution ports 114 into and/or proximate the target tissue. Similarly, distal movement of slide button 116 relative to handle body 112 causes distal movement of tube 140 to interrupt fluid communication between fluid distribution ports 114 and fluid channel 134 from a proximal end thereof toward a distal end thereof. In this manner, a user may manipulate the slide button 116 relative to the handle body 112 to control the placement of cooling fluid and/or steam as desired or depending on the size of the ablation. In some embodiments, the fluid distribution ports 114 may be microporous, macroporous, or any combination thereof. The higher the porosity, the more freely the cooling fluid 31 will flow through the outer jacket 108. The fluid distribution ports 114 may be defined through the outer jacket 108 along the entire length thereof. Alternatively, the fluid distribution ports 114 may only be defined through the portion of the outer jacket 108 that will be adjacent the ablation region (e.g., a distal end of the radiating portion 106). The cooling fluid 31 flows outwardly through the fluid distribution ports 114 as shown by the arrows extending outwardly therefrom. Alternatively, one or more of the fluid distribution ports 114 may be defined at an angle with respect to the surface of the outer jacket 108 (not explicitly illustrated) such that the cooling fluid 31 may flow outwardly in various radial directions (e.g., proximal, distal, etc.).

In some embodiments, cooling assembly 100 may include passive-type plugs or seals (not explicitly shown) to passively seal each fluid distribution port 114. The seals may be expanded outward by positive fluid pressure communicated through the fluid distribution ports 114 to allow cooling fluid 31 to be expelled from the cooling assembly 100. In this way, cooling fluid 31 may remain circulated within the fluid channel 134 until the supply pump 40 creates additional positive fluid pressure to expand the seals outward, thereby permitting cooling fluid 31 to exit the fluid channel 134 via the fluid distribution ports 114.

In some embodiments, the cooling assembly 100 may be configured to selectively inject cooling fluid 31 into the surrounding tissue through any one or more specific fluid distribution ports 114. That is, cooling fluid 31 may be injected into the surrounding tissue from any port or group of ports positioned about the circumference of the outer jacket 108. In this configuration, the cooling assembly 100 may include one or more additional inflow tubes (not explicitly shown) in direct fluid communication with a specific port or specific group of ports. As such, the controller 34 may cause the supply pump 40 to pump cooling fluid 31 through specific inflow tubes and/or specific groups of inflow tubes into and/or proximate the surrounding tissue via specific ports or specific groups of ports. In this way, cooling fluid 31 may be targeted proximally, distally, or in a specific radial direction.

Figure 4C:
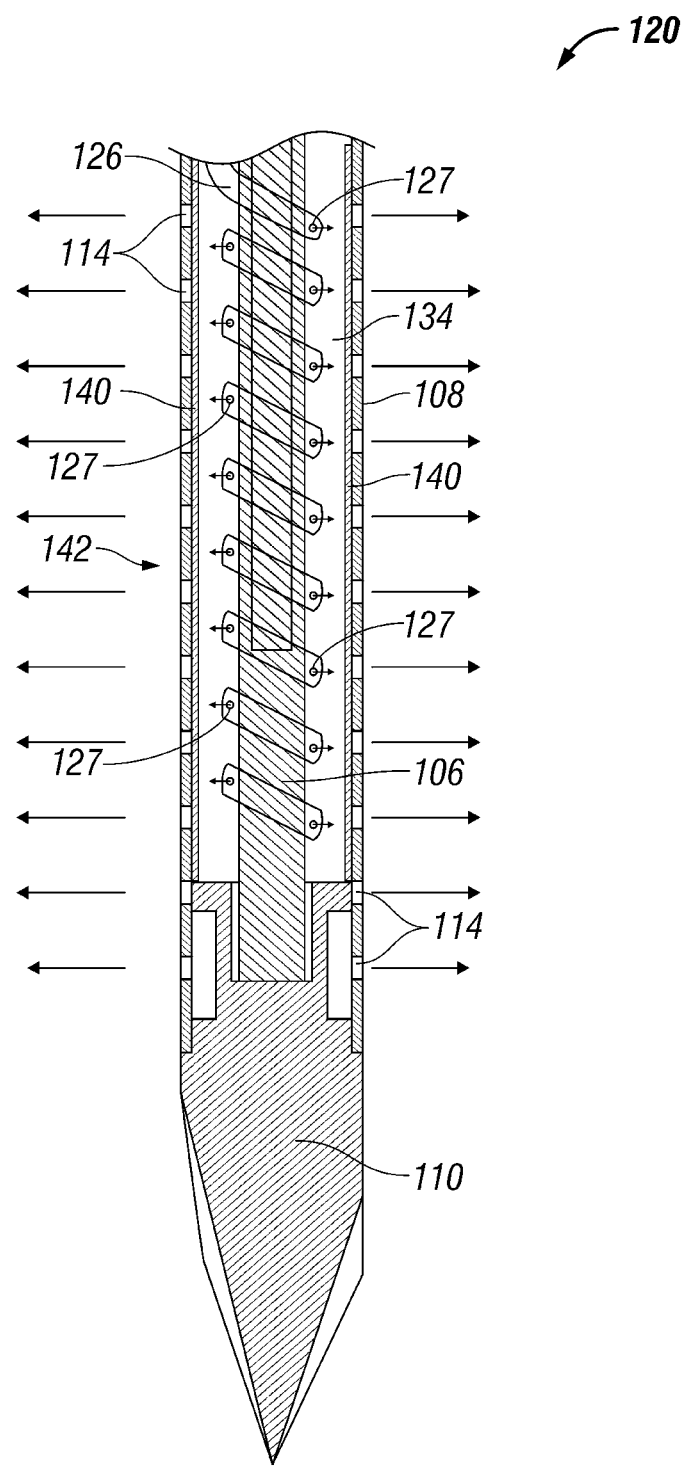
FIGS. 4C and 4D are alternative embodiments of the area of detail of the microwave antenna shown in FIG. 4B.

FIG. 4C shows an alternative embodiment of inlet tube 126 shown as a helical shape extending distally through outer jacket 108. In this configuration, inlet tube 126 is in contact with the radiating portion 106 to facilitate faster heating of the cooling fluid within inlet tube 126 such that steam may be expelled from a plurality of ports 127 disposed through inlet tube 126.

Figure 4D:
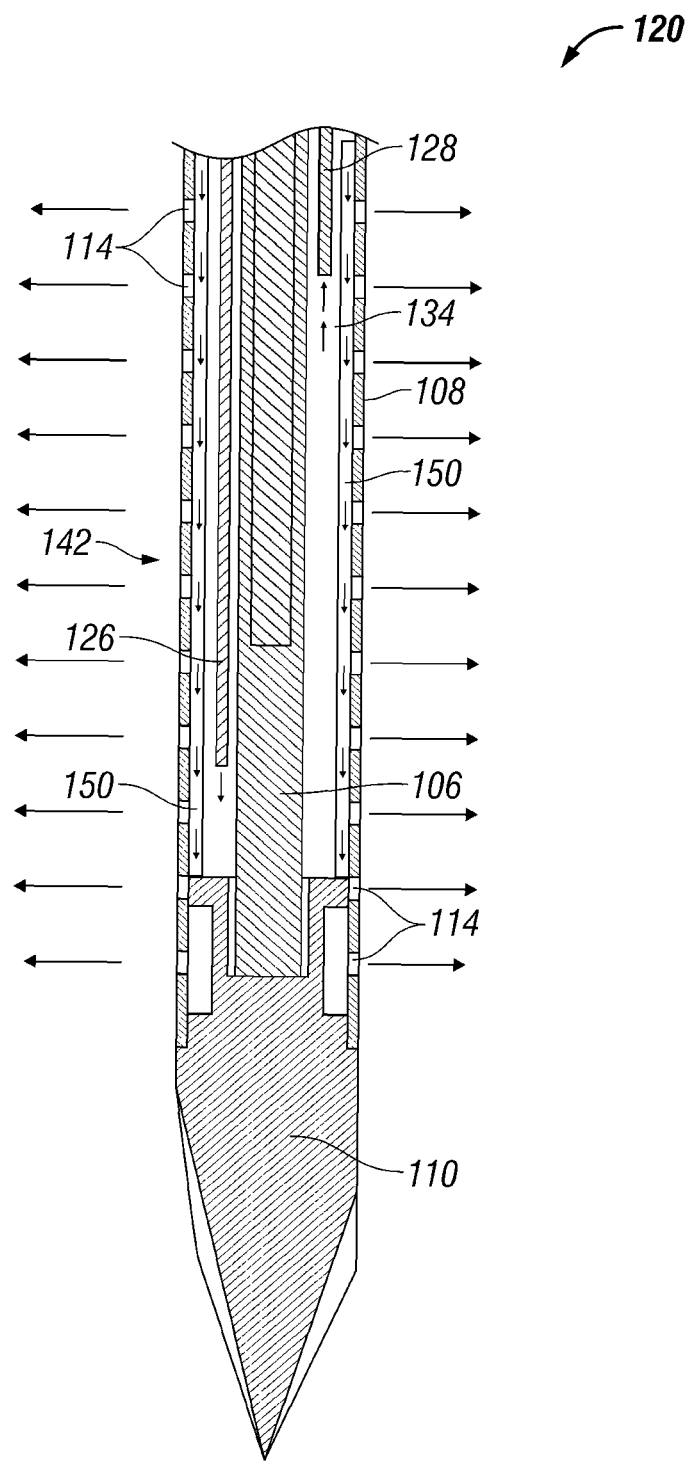

In some embodiments, as shown in FIG. 4D, one or more infusion inlet tubes 150 may be disposed coaxially through outer jacket 108 to provide infusion fluid (not shown) directly from the supply pump 40, as opposed to cooling fluid 31 supplied via inlet tube 126, such that infusion fluid and cooling fluid circulate separately within the antenna assembly 10. In this scenario, additional inflow tubing (not shown) is disposed in fluid communication between the supply pump 40 and infusion inflow tubes 150 and supplies infusion fluid to the infusion inflow tubes 150 using positive pressure from the supply pump 40. Infusion inlet tubes 150 are in fluid communication with one or more fluid distribution ports 114 such that positive pressure from the supply pump 40 causes the infusion fluid in the infusion inflow tubes 150 to be expelled from one or more fluid distribution ports 114 and into and/or proximate the target tissue. The embodiment in FIG. 4D may be particularly suitable for radiofrequency ablation.

Figure 5:
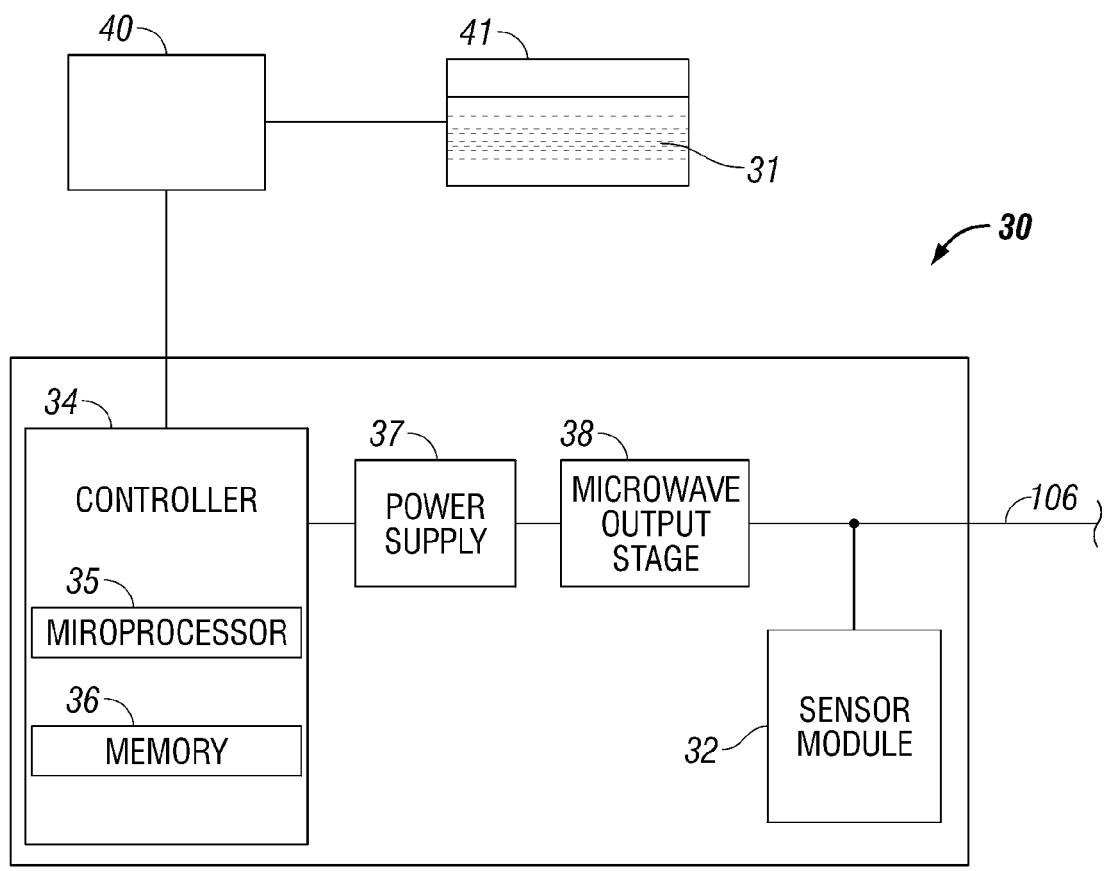
FIG. 5 is a schematic block diagram of a generator control system according to one embodiment of the present disclosure.

FIG. 5 shows a schematic block diagram of the generator 30 operably coupled to the supply pump 40. The supply pump 40 is, in turn, operably coupled to the supply tank 41. The generator 30 includes a controller 34, a power supply 37, a microwave output stage 38, and a sensor module 32. The power supply 37 provides DC power to the microwave output stage 38 which then converts the DC power into microwave energy and delivers the microwave energy to the radiating portion 106. The controller 34 includes a microprocessor 35 having a memory 36 which may be volatile type memory (e.g., RAM) and/or non-volatile type memory (e.g., flash media, disk media, etc.). The microprocessor 35 includes an output port connected to the supply pump 40, which allows the microprocessor 35 to control the output of cooling fluid 31 from the supply pump 40 to the cooling assembly 100 according to either open and/or closed control loop schemes. In the illustrated embodiment, the microprocessor 35 also includes an output port connected to the power supply 37 and/or microwave output stage 38 that allows the microprocessor 35 to control the output of the generator 30 according to either open and/or closed control loop schemes. Further, the cooling assembly 100 may include suitable input controls (e.g., buttons, activators, switches, etc.) for manually controlling the output of the supply pump 40. Specifically, the input controls may be provided with leads (or wireless) for transmitting activation signals to the controller 34. The controller 34 then signals the supply pump 40 to control the output of cooling fluid 31 from the supply tank 41 to the cooling assembly 100. In this way, clinicians may manually control the supply pump 40 to cause cooling fluid 31 to be expelled from the cooling assembly 100 into and/or proximate the surrounding tissue.

A closed loop control scheme generally includes a feedback control loop wherein the sensor module 32 provides feedback to the controller 34 (i.e., information obtained from one or more sensing mechanisms for sensing various tissue and/or antenna parameters, such as tissue impedance, antenna impedance, tissue temperature, antenna temperature, output current and/or voltage, etc.). The controller 34 then signals the supply pump 40 to control the output thereof (e.g., the volume of cooling fluid 31 pumped from the supply tank 41 to the cooling assembly 100). The controller 34 also receives input signals from the input controls of the generator 30 and/or antenna assembly 10. The controller 34 utilizes the input signals to adjust the cooling fluid 31 output of the supply pump 40 and/or the power output of the generator 30.

The microprocessor 35 is capable of executing software instructions for processing data received by the sensor module 32, and for outputting control signals to the generator 30 and/or supply pump 40, accordingly. The software instructions, which are executable by the controller 34, are stored in the memory 36 of the controller 34.

The controller 34 may include analog and/or logic circuitry for processing the sensed values and determining the control signals that are sent to the generator 30 and/or supply pump 40, rather than, or in combination with, the microprocessor 35. The sensor module 32 may include a plurality of sensors (not explicitly shown) strategically located for sensing various properties or conditions, e.g., tissue impedance, antenna impedance, voltage at the tissue site, current at the tissue site, tissue temperature, antenna temperature, etc. The sensors are provided with leads (or wireless) for transmitting information to the controller 34. The sensor module 32 may include control circuitry that receives information from multiple sensors, and provides the information and the source of the information (e.g., the particular sensor providing the information) to the controller 34.

When coupling electromagnetic radiation such as microwaves from a source to an applicator, in order to maximize the amount of energy transferred from the source (microwave generator) to the load (surgical implement), the line and load impedances should match. If the line and load impedances do not match (e.g., an impedance mismatch) a reflected wave may be created that can generate a standing wave, which contributes to a power loss associated with the impedance mismatch. As used herein, "load impedance" is understood to mean the impedance of the radiating portion 12 and "line impedance" is understood to mean the impedance of the feedline 14.

In some embodiments, the controller 34 is configured to control the cooling fluid 31 output from the supply pump 40 to the antenna assembly 10 based on a reflectance parameter, such as a mismatch detected between the load impedance and the line impedance. Such an impedance mismatch may cause a portion of the power, so called "reflected power," from the generator 30 to not reach the tissue site and cause the power delivered, the so called "forward power," to vary in an irregular or inconsistent manner. It is possible to determine the impedance mismatch by measuring and analyzing the reflected and forward power. In particular, the generator 30 measures energy delivery properties, namely the forward power, and dynamically adjusts the cooling fluid 31 output of the supply pump 40 to compensate for a detected mismatch between the line impedance and the load impedance. That is, upon detection of an impedance mismatch, additional cooling fluid 31 is pumped through inflow tubing 19 and into the fluid channel 134 using positive pressure from the supply pump 40. This positive pressure causes additional fluid pressure in the fluid channel 134, which in turn, causes cooling fluid 31 to flow through the fluid distribution ports 114 (e.g., by expanding the seals outward) into and/or proximate the surrounding tissue. In this manner, the cooling fluid 31 effectively re-hydrates surrounding tissue to generate additional steam. This generation of additional steam allows for the transfer of heat away from the target tissue site for the duration of the procedure. The resulting drop in tissue temperature (or more specifically, a change in a dielectric constant e1 of the tissue surrounding the antenna) effectively lowers the load impedance to match the line impedance, thereby optimizing energy delivery to the target tissue site. Other reflectance parameters include reflectance coefficient, standing wave ratio (SWR), and reflectance loss.

In operation, the sensor module 32 is coupled to the microwave output stage 37 and is configured to measure a reflectance parameter. The sensor module 32 may include one or more directional couplers or other voltage and current sensors that may be used to determine voltage and current measurements as well as the phase of the voltage and current waveforms. The voltage and current measurements are then used by the sensor module 32 to determine the reflectance parameter. The sensor module 32 converts the measured parameter into corresponding low level measurement signals (e.g., less than 5 V) which are transmitted to the controller 34.

The controller 34 accepts one or more measurements signals indicative of power delivery, namely, the signals indicative of the reflectance parameter. The controller 34 analyzes the measurement signals and determines an impedance mismatch based on the reflectance parameter. The controller 34 thereafter determines whether any adjustments to the output of the supply pump 40 have to be made to adjust (e.g., re-hydrate) the surrounding tissue to compensate for the mismatch in impedance based on the reflectance parameter. Additionally, the controller 34 may also signal the microwave output stage 38 and/or the power supply 37 to adjust output power based on the reflectance parameter.

Figure 6:
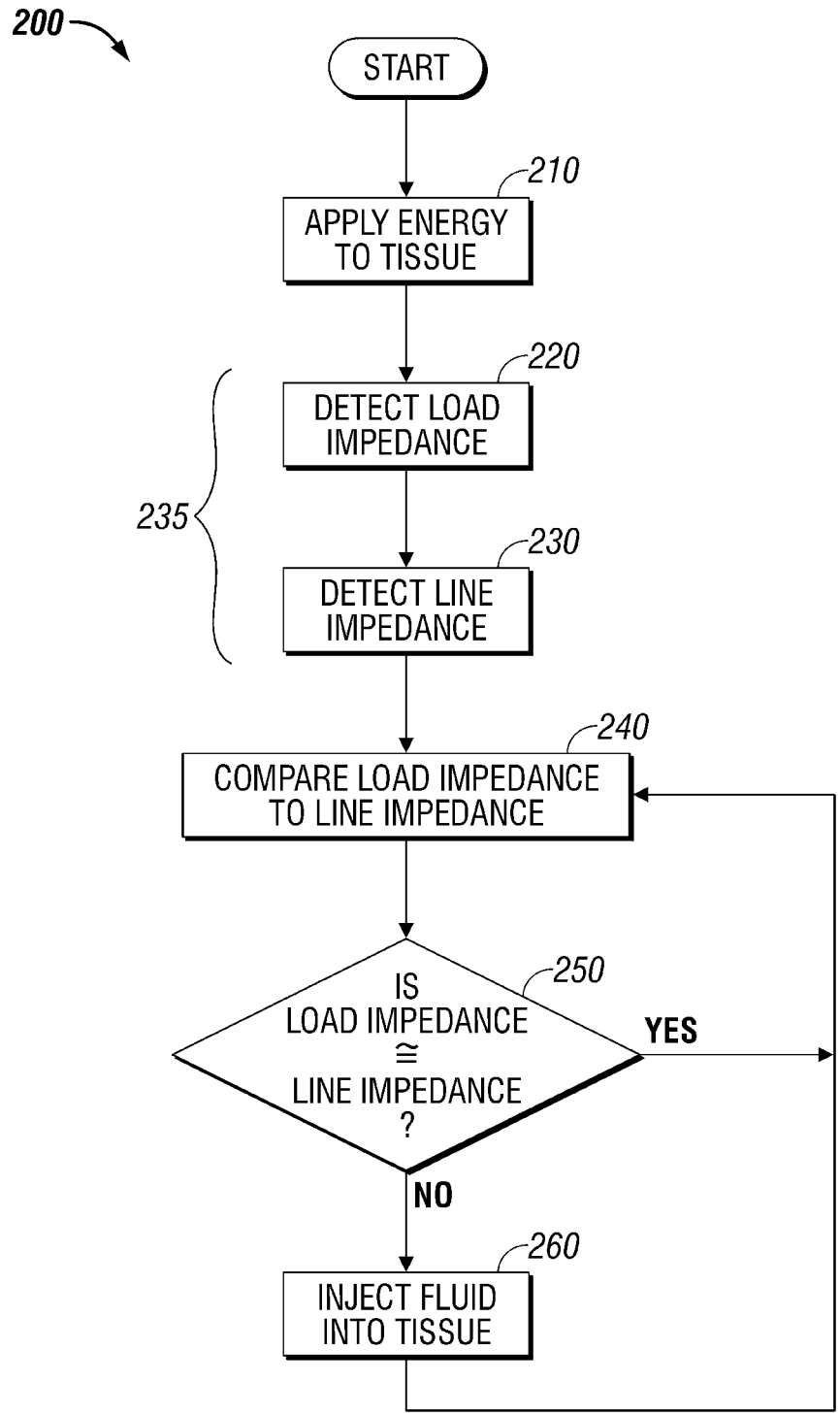
FIG. 6 is a flowchart diagram showing one method for hydrating tissue undergoing treatment according to the present disclosure.

FIG. 6, in conjunction with FIGS. 3, 4A, 4B, and 5, illustrates a method 200 for selectively re-hydrating tissue undergoing treatment according to one embodiment. In step 210, energy from the generator 30 is applied to tissue via the antenna 104 to heat a target treatment area. In step 235, one or more reflectance parameters are detected by the sensor module 32 (e.g., using sensors) and communicated to the controller 34 for storage in the memory 36. In the illustrated embodiment, the reflectance parameters detected in step 235 include a load impedance (detected in step 220) and a line impedance (detected in step 230). In step 240, the microprocessor 35 compares the load impedance to the line impedance. If the load impedance and the line impedance are not at least substantially equivalent in step 250, the microprocessor 35 outputs a control signal to the supply pump 40 in step 260 to cause cooling fluid 31 to be expelled from the cooling assembly 100 into and/or proximate the surrounding tissue. If the load impedance and line impedance are substantially equivalent in step 250, step 240 is repeated. The method 200 may loop continuously throughout the duration of the procedure to re-hydrate the target tissue and generate additional steam as a heat transfer mechanism. The resulting drop in tissue temperature (or change in dielectric constant e1 of the tissue surrounding the antenna) acts to improve energy delivery to the target tissue by facilitating an impedance match between the line and the load.

Figure 7:
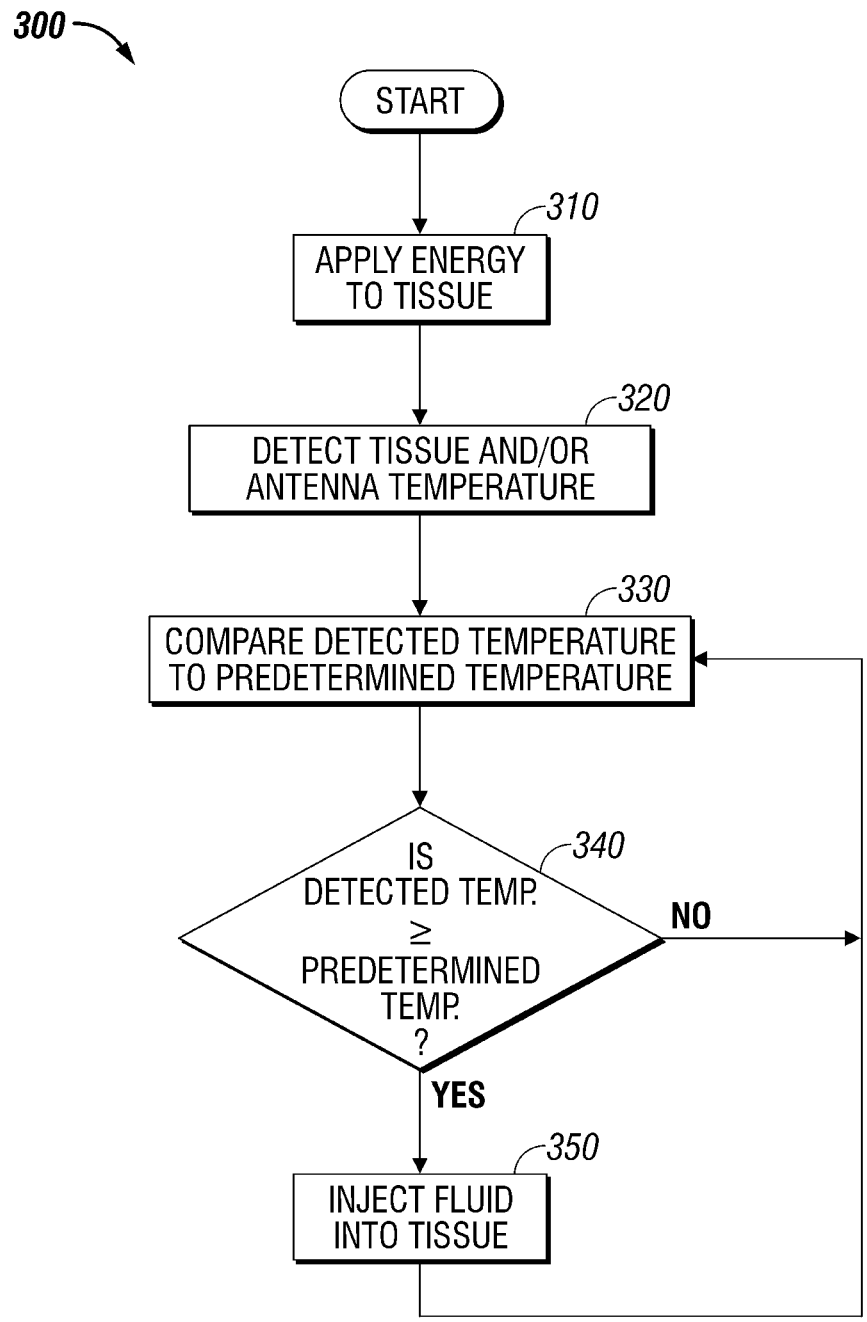
FIG. 7 is a flowchart diagram showing another method for hydrating tissue undergoing treatment according to the present disclosure.

FIG. 7, in conjunction with FIGS. 3, 4A, 4B, and 5, illustrates a method 300 for selectively re-hydrating tissue undergoing treatment according to another embodiment. In step 310, energy from the generator 30 is applied to tissue via the antenna 104 to heat a target treatment area. In step 320, a tissue temperature and/or an antenna temperature is detected by the sensor module 32 (e.g., using an optical temperature sensor) and communicated to the controller 34 for storage in the memory 36. In step 330, the microprocessor 35 compares the detected temperature to a predetermined temperature (e.g., about 104° C.). If the detected temperature is greater than or equal to the predetermined temperature in step 340, the microprocessor 35 outputs a control signal to the supply pump 40 in step 350 to cause cooling fluid to be expelled from the cooling assembly 100 into and/or proximate the surrounding tissue. If the detected temperature is less than the predetermined temperature in step 340, step 330 is repeated. The method 300 may loop continuously throughout the duration of the procedure to re-hydrate the target tissue and generate additional steam as a heat transfer mechanism. The resulting drop in tissue temperature acts to improve energy delivery by maintaining the target tissue site at a temperature below a temperature at which significant tissue dehydration may occur.

In some embodiments, the disclosed methods may be extended to other tissue effects and energy-based modalities including, but not limited to, ultrasonic and laser tissue treatments. The methods 200 and 300 are based on impedance measurement and monitoring and temperature measurement and monitoring, respectively, but other tissue and energy properties may be used to determine state of the tissue, such as current, voltage, power, energy, phase of voltage and current. In some embodiments, the method may be carried out using a feedback system incorporated into an electrosurgical system or may be a stand-alone modular embodiment (e.g., removable modular circuit configured to be electrically coupled to various components, such as a generator, of the electrosurgical system).

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A microwave ablation device, comprising:
a handle body;
a microwave antenna operatively coupled to the handle body;
a cable connector configured to connect the microwave antenna in electrical communication to an energy source via a feedline;
an outer jacket surrounding the microwave antenna to define a fluid volume, the outer jacket defining a plurality of fluid distribution ports in fluid communication with the fluid volume and configured to permit a flow of fluid into surrounding tissue of a patient;
at least one inflow tubing in fluid communication with the fluid volume defined by the microwave antenna and the outer jacket; and
a helical-shaped inlet tube encircling at least a portion of the microwave antenna, the helical-shaped inlet tube in fluid communication with the at least one inflow tubing and the fluid volume.

2. The microwave ablation device according to claim 1, further comprising a temperature sensor configured to detect a temperature of the microwave antenna.

3. The microwave ablation device according to claim 2, wherein the temperature sensor provides a feedback signal that is used to control operation of the energy source.

4. The microwave ablation device according to claim 1, further comprising a temperature sensor configured to detect a temperature of a patient's tissue adjacent the microwave antenna.

5. The microwave ablation device according to claim 1, further comprising a sensor module in communication with the energy source and configured to detect a reflectance parameter based on energy applied to tissue by the microwave antenna.

6. The microwave ablation device according to claim 5, wherein the sensor module provides feedback to the energy source based on the detected reflectance parameter to control operation of the energy source.

7. The microwave ablation device according to claim 1, wherein the microwave antenna extends proximally through at least a portion of the handle body.

8. The microwave ablation device according to claim 1, wherein the helical-shaped inlet tube includes a plurality of ports in fluid communication with the fluid volume.

9. The microwave ablation device according to claim 1, further comprising an outflow tube coupled to the handle body and configured to return cooling fluid from the fluid volume to a cooling fluid source.

10. A microwave ablation system, comprising:
an energy source; and
a microwave antenna assembly comprising:
a handle body;
a microwave antenna operatively coupled to the handle body;
a cable connector configured to connect the microwave antenna in electrical communication to the energy source via a feedline;
an outer jacket surrounding the microwave antenna to define a fluid volume, the outer jacket defining a plurality of fluid distribution ports in fluid communication with the fluid volume and configured to permit a flow of fluid into surrounding tissue of a patient;
at least one inflow tubing in fluid communication with the fluid volume defined by the microwave antenna and the outer jacket; and
a helical-shaped inlet tube encircling at least a portion of the microwave antenna, the helical-shaped inlet tube in fluid communication with the at least one inflow tubing and the fluid volume.

11. The microwave ablation system according to claim 10, wherein the microwave antenna assembly further comprises a temperature sensor configured to detect a temperature of the microwave antenna.

12. The microwave ablation system according to claim 11, further comprising a controller, wherein the temperature sensor provides a feedback signal to the controller to control operation of the energy source based at least in part on the feedback signal.

13. The microwave ablation system according to claim 10, wherein the microwave antenna extends proximally through at least a portion of the handle body.

14. The microwave ablation system according to claim 10, further comprising a cooling fluid source configured to circulate cooling fluid through the microwave antenna.

15. The microwave ablation system according to claim 10, wherein the helical-shaped inlet tube of the microwave antenna assembly includes a plurality of ports in fluid communication with the fluid volume.

16. The microwave ablation system according to claim 10, further comprising an outflow tube coupled to the handle body and configured to return cooling fluid from the fluid volume to a cooling fluid source.

* * * * *